United States Patent [19]

Brucks et al.

[11] Patent Number: 5,720,948
[45] Date of Patent: Feb. 24, 1998

[54] NON-IONIC SURFACTANT EMULSION VEHICLES AND THEIR USE FOR DEPOSITION OF DRUG INTO AND ACROSS SKIN

[75] Inventors: Richard M. Brucks, Chicago; Lane A. Duvel, Carol Stream, both of Ill.

[73] Assignee: Helene Curtis Inc., Chicago, Ill.

[21] Appl. No.: 553,205

[22] Filed: Nov. 7, 1995

[51] Int. Cl.$^6$ .................................................. A61K 31/74
[52] U.S. Cl. .................................... 424/78.02; 424/78.03; 424/78.04; 514/912
[58] Field of Search ......................... 424/78.02, 78.03, 424/78.04; 514/912

[56] References Cited

U.S. PATENT DOCUMENTS

| | | | |
|---|---|---|---|
| 4,380,549 | 4/1983 | Van Scott et al. | 424/317 |
| 4,483,867 | 11/1984 | Svahn et al. | 424/279 |
| 5,073,372 | 12/1991 | Turner et al. | 424/401 |

FOREIGN PATENT DOCUMENTS

| | | | |
|---|---|---|---|
| 0585130 | 3/1994 | European Pat. Off. | A61K 7/48 |
| 6-9366 | 1/1994 | Japan | A61K 7/48 |
| 6-65053 | 3/1994 | Japan | A61K 7/48 |
| 6-80554 | 3/1994 | Japan | A61K 7/48 |
| 6192066 | 7/1994 | Japan | A61K 9/127 |
| 6279316 | 10/1994 | Japan | A61K 37/64 |
| WO9402444 | 2/1994 | WIPO | C07C 299/46 |

OTHER PUBLICATIONS

Chiang, Chia-Ming et al., "Bioavailability assessment of topical delivery systems: Effect of vehicle evaporation upon in vitro delivery of minoxidil from solution formulations," *Int. J. Pharm.* 55: 229–36 (1986).

Dupin, J.P. et al., "Investigation and determination of the antifibrinolytic properties of dipeptides and synthetic compounds," *Path. Biol.* 26 (5): 233–39 (1978).

Fleisher, D. et al., "Topical delivery of growth hormone releasing peptide using liposomal systems: An in vitro study using hairless mouse skin," *Life Sciences* 57 (13): 1293–97 (1995).

Ganesan, M.G. et al., "Influence of liposomal drug entrapment on percutaneous absorption" *Int. J. Pharm.* 20: 139–54 (1984).

Ho, N.F.H. et al., "Mechanisms of topical delivery of liposomally entrapped drugs," *J. Controlled Release* 2: 61–65 (1985).

Isoda, S. and M. Harata, "Medicinal chemical studies on antiplasmin drugs. III. 4—aminomethylcyclohexanecarboxylic acid and its derivatives having a methyl group," *Chem. Pharm. Bull.* 27(11): 2735–42 (1979).

Junginger, H.E. et al., "Liposomes and niosomes: Interactions with human skin," *Cosmetics & Toiletries* 106: 45–50 (1991).

Kitamura, K. et al., "Research on the mechanism by which dry skin occurs and the development of an effective compound for its treatment," *18th Int. IFSCC Congress* 1: 131–66 (1994).

Lieb, L.M. et al., "Topical delivery enhancement with multilamellar liposomes into pilosebaceous units: I. In vitro evaluation using fluorescent techniques with the hamster ear model," *J. Invest. Dermatol.* 99(1): 108–13 (1992).

Lieb, L.M. et al., "Follicular (pilosebaceous unit) deposition and pharmacological behavior of cimetidine as a funciton of formulation," *Pharm. Res.* 11(10): 1419–23 (1994).

Markwardt, F., "Synthetic inhibitors of fibrinolysis," *Progress in Fibrinolysis* 5:178–83 (1981).

Okano, A. et al., "Medicinal chemical studies on antiplasmin drugs. 4. Chemical modification of trans–4–aminomethylcyclohexanecarboxylic acid and its effect on antiplasmin activity," *J. Med. Chem.* 15(3): 247–55 (1972).

Schreier H. and J. Bouwstra, "Liposomes and niosomes as topical drug carriers:Dermal and transdermal drug delivery," *J. Controlled Release* 30: 1–15 (1994).

Svahn, C.M. et al., "Tranexamic acid derivatives with enhanced absorption," *J. Med. Chem.* 29(4): 448–53 (1986).

Takeshita, T. et al., "A facile synthesis of aminocarboxylic acid derivatives, new anti–ulcer agents," *Chem. Pharm. Bull.* 33(11): 5059–61 (1985).

Tata, S. et al., "Relative influence of ethanol and propylene glycol cosolvents on deposition of minoxidil into the skin," *J. Pharm. Sci.* 83(10): 1508–10 (1994).

Tata, S. et al., "Penetration of minoxidil from ethanol/ propylene glycol solutions: Effect of application vol. and occlusion," *J. Pharm. Sci.* 84(6): 688–91 (1995).

Tsai, J.-C. et al., "Solvent effects on the harvesting of stratum corneum from hairless mouse skin through adhesive tape stripping in vitro," *Int. J. Pharm.* 68: 127–23 (1991).

Tsai, J.-C. et al., "Drug and vehicle deposition from topical applications: Use of in vitro mass balance technique with minoxidil solution," *J. Pharm. Sci.* 81(8): 736–43 (1992).

Tsai, J.-C. et al., "Effect of minoxidil concentration on the deposition of drug and vehicle into the skin," *Int. J. Pharm.* 96: 111–17 (1993).

Tsai, J.-C. et al., "Drug and vehicle deposition from topical applications: localization of minoxidil within skin strata of the hairless mouse," *Skin Pharmacol.* 7: 262–69 (1994).

Tsai, J.-C. et al., "Influence of application time and formulation reapplication on the delivery of minoxidil through hairless mouse skin as measured in Franz diffusion cells," *Skin Pharmacol.* 7: 270–77 (1994).

Walters, K.A. et al., "Non–ionic surfactant effects on hairless mouse skin permeability characteristics," *J. Pharm. Pharmacol.* 40: 525–29 (1988).

(List continued on next page.)

*Primary Examiner*—Zohreh Fay
*Attorney, Agent, or Firm*—Milton L. Honig

[57] ABSTRACT

Non-ionic surfactant emulsion vehicles and compositions comprising an emulsifier system including one or more non-ionic surfactants, an oil phase and an aqueous phase for enhancing the penetration of a drug substance across the stratum corneum and into deeper skin layers are disclosed. A method whereby an effective amount of a composition comprising the emulsion vehicle and a drug substance is topically applied to the skin also is disclosed.

8 Claims, No Drawings

OTHER PUBLICATIONS

Yoshioka, T. et al., "Preparation and properties of vesicles (niosomes) of sorbitan monoesters (Span 20, 40, 60 and 80) and a sorbitan triester (Span 85)," *Int. J. Pharm.* 105: 1–6 (1994).

The HLB SYSTEM, a time–saving guide to emulsifier selection, ICI Americas Inc. (Wilmington, Delaware), pp. 1–17, 1984.

Chemical Abstracts 106:38372 (1986). Aungst et al.

NON-IONIC SURFACTANT EMULSION VEHICLES AND THEIR USE FOR DEPOSITION OF DRUG INTO AND ACROSS SKIN

FIELD OF THE INVENTION

This invention generally relates to enhancing the penetration of drug substances across the skin, and more particularly, to a delivery vehicle used to achieve deposition of drugs including plasminogen activator inhibitors into and through the skin.

BACKGROUND OF THE INVENTION

One of the main disadvantages in topical drug delivery is the low penetration rate of drug substances through the skin. Several techniques have been investigated to increase the drug penetration rate across skin including penetration enhancers and liposomes. Liposomes, however, in and of themselves do not diffuse across intact skin. Schreier & Bouwstra, *J. Controlled Release* 2:61–65 (1984).

The effectiveness of delivering a drug substance across the skin can be increased by altering the barrier properties of the outermost layer of the skin, the stratum corneum. Alternatively, the penetration rate can be improved by increasing the ability of the drug to partition out of the vehicle. Compounds which can effectively alter the barrier properties of the stratum corneum, collectively known as penetration enhancers, vary widely in their structure and thus imply that the mechanisms of action are complex and may involve different routes of permeation through the skin. Walters et al., *J. Phar. Pharmacol.* 40:525–29 (1988).

Liposomes are formed from phospholipids. Niosomes, which may be considered a special case of liposomes, are prepared from non-ionic surfactants such as polyoxyethylene alkylether, polyoxyethylene alkylester or saccharose diester. An essential component of liposomes and niosomes is cholesterol (CHO). It is believed that cholesterol is instrumental in forming the vesicles and contributes to the stability of the vesicular structures after they have been formed.

Under normal conditions, the skin maintains balanced growth through the proliferation, differentiation and stratification of epidermal basal cells. This process continually replaces the skin's surface cells as they spontaneously shed or are lost as a consequence of environmental insults. It is believed that the plasminogen activator (PA)/plasminogen activator inhibitor (PAI) system plays a key role in modulating the skin's biological equilibrium. Kitamura et al., *IFSCC* (Venezia) 131–166 (1994).

Thus, there is a need for providing stable delivery vehicles and methods for use therein by which drug substances, and in particular, PAI compounds, can be transported more effectively across the stratum corneum and into deeper skin layers.

SUMMARY OF THE INVENTION

One aspect of the present invention relates to a non-ionic surfactant emulsion vehicle comprising an emulsifier system including one or more non-ionic surfactants, an oil phase and an aqueous phase.

Another aspect of the present invention relates to a composition for enhancing the penetration of a drug substance across the stratum corneum and into deeper skin layers comprising an emulsifier system including one or more non-ionic surfactants, an oil phase, an aqueous phase and a drug substance. More particularly, the invention relates to a composition for enhancing the penetration of plasminogen activator inhibitors across the stratum corneum and into deeper skin layers comprising an emulsifier system including one or more non-ionic surfactants, an oil phase, an aqueous phase and at least one plasminogen activator inhibitor compound such as tranexamic acid, epsilon-amino caproic acid, p-aminomethylbenzoic acid and other ω-aminocarboxylic acids.

Still another aspect of the present invention relates to a method by which a composition comprising a delivery vehicle of the present invention is applied to an external portion of the body and enhances the penetration of a drug substance across the stratum corneum and into deeper layers of the skin. In particular, the method comprises the steps of providing a composition comprising an emulsifier system including one or more non-ionic surfactants, an oil phase, an aqueous phase and a drug substance, and topically applying an effective amount of the composition to the skin.

Advantages associated with the present invention include the discovery that non-ionic surfactants can be used to prepare emulsions which enhance the penetration of drug substances into the skin without the use of liposomes. Furthermore, in contrast to liposome vehicles, cholesterol is not needed to provide stable emulsion vehicles, and because we have shown that cholesterol inhibits drug penetration, the delivery vehicles of the present invention increase the drug penetration rate across skin. Moreover, the delivery vehicles of the present invention enhance the penetration of drug substances across the stratum corneum and into deeper skin layers.

DETAILED DESCRIPTION OF THE INVENTION

The term "delivery vehicle," or simply "vehicle," as used herein refers to a system of carrier molecules used to deliver or deposit a drug substance into and through the skin.

The term "Emulsifier System" as used herein refers to a set of one or more non-ionic surfactants used to emulsify an oil in the vehicles of the present invention. The term "GDL Emulsifier System" as used herein specifically refers to the emulsifier system of glyceryl dilaurate (GDL) and polyoxyethylene-10 stearyl ether (POE-10). Such a system may include a certain ratio of GDL and POE-10 as discussed below.

The term "Emulsion Ratio" as used herein refers to the ratio of the emulsifier system (Emul) including one or more non-ionic surfactants to the oil phase (Oil) to the aqueous phase (Aq).

It has been discovered that delivery vehicles comprising an emulsifier system including one or more non-ionic surfactants provide stable compositions without the addition of cholesterol to the formulation. We also have discovered that cholesterol in delivery vehicle formulations inhibits drug penetration. Thus, the delivery vehicles of the present invention provide the added benefit of increasing the drug penetration rate across skin. It is believed that the surfactants possibly penetrate into the stratum corneum thereby enhancing drug penetration.

The non-ionic surfactant emulsifier system used in the delivery vehicles of the present invention is designed to more effectively penetrate the stratum corneum and deliver the drug substance into the deeper skin layers. The emulsifier system may be designed around one or more non-ionic surfactants such as polyoxyethylene alkylethers, polyoxyethylene alkylesters, glyceryl di-esters, sorbitan di-esters and sorbitan tri-esters and their structural equivalents.

In general, polyoxyethylene alkylethers having the general formula HO—CH$_2$—CH$_2$—[—O—CH$_2$—CH$_2$—]$_n$—O—R, wherein R=fatty alcohols C$_8$–C$_{22}$ and n=2–100, and more preferably R=fatty acid alcohols C$_{12}$–C$_{18}$ and n=2–20, and polyoxyethylene alkylesters having the general formula HO—CH$_2$—CH$_2$—[—O—CH$_2$—CH$_2$—]$_n$—O—CO—R, wherein R=fatty acids C$_8$–C$_{12}$ (saturated or unsaturated) and n=2–100, and more preferably R=fatty acids C$_{12}$–C$_{18}$ and n=2–20, are useful in the delivery vehicles of the present invention.

When the emulsifier system is made up of one or more non-ionic surfactants, the optimal ratio of one surfactant to another can be determined by one of ordinary skill in the art through routine experimentation by obtaining penetration profiles on trial emulsions and determining which ratio of non-ionic surfactants as well as the concentration of the emulsifier system maximizes the penetration of the drug substance across the stratum corneum and into the deeper skin layers. The penetration profiles can be carried out in vitro or in vivo. In the in vitro studies, skin sections excised from hairless mice and from which the subcutaneous fat has been removed are mounted on Franz diffusion cells. The dermal side of the skin is placed in contact with receiver medium and the trial emulsion is applied to the epidermal surface of the skin. In the in vivo studies, the trial emulsion is applied to the skin of live, anesthetized hairless mice for a certain time period typically ranging from about 4 to about 12 hours, then the skin is excised, the subcutaneous fat is removed and the excised skin section is mounted on a wooden board. For both the in vitro and in vivo experiments, the skin surface is stripped with adhesive tape until the skin has a glossy appearance indicating the complete removal of the stratum corneum. The various skin sections are assayed to determine the amount of radiolabeled drug. Tata et al., *J. Pharm. Sci.* 84:688–91 (1995), the "Methods" section of which is incorporated herein by reference.

Other factors to consider when optimizing the emulsifier system include stability, opacity, viscosity, ease of preparation and ease of application. The particular emulsifier ratio may vary based on the particular oil and drug substance chosen for the emulsion but can be determined based on known procedures in the emulsion art. See, e.g., "The HLB [Hydrophile-Lipophile Balance] System," published by ICI Americas Inc., Wilmington, Del., 1984, which is incorporated herein by reference in its entirety.

In a preferred embodiment of the delivery vehicles of the invention, the emulsifier system comprises the non-ionic surfactants glyceryl dilaurate and polyoxyethylene-10 stearyl ether. In addition, no cholesterol is used in the emulsifier system. With respect to the so-called GDL Emulsifier System, the GDL:POE-10 ratio ranges from about 5:95 to about 75:25, more preferably from about 20:80 to about 40:60, and most preferably from about 20:80 to about 45:55. In an especially preferred embodiment, the GDL:POE-10 ratio is 20:80.

The oil phase for use in formulating the vehicles of the present invention can comprise one or more oils selected from cosmetically-acceptable oils well known to one of ordinary skill in the art. The kinds of oils that can be emulsified include mineral oils such as light mineral oil, natural oils such as safflower and soybean oils, hydrocarbon oils, silicone oils such as dimethicone, volatile silicone oils such as cyclomethicone, and derivatives of naturally occurring fatty acids, for example, esters such as isopropyl myristate, isopropyl palmitate and cetyl octanoate, and more particularly, glyceryl esters such as caprylic/capric glycerides. The particular oil (or oils) chosen is partly based on the form of the composition, such as, for example, hand lotion or cream.

As is known to one of ordinary skill in the art, each oil to be incorporated into the emulsion vehicles of the invention has an individual "Required HLB." Thus, the ratio of emulsifiers used may have to be changed in order to provide stable emulsions based on the particular oils included in the emulsion vehicles.

The aqueous phase of the delivery vehicles of the present invention may be prepared without using any buffers. Alternatively, a buffer system may be included as part of the aqueous phase in the vehicles. Whether or not a buffer is included as part of the aqueous phase has no effect on the penetration enhancer potential of the vehicle. Rather, whether a buffer system is included is left to the discretion of the ordinary practitioner. If a buffer system is preferred, a buffer system such as 0.05M isotonic HEPES buffer, pH 7.4, can be used.

The non-ionic surfactant emulsion vehicles of the present invention comprise 1) an emulsifier system including one or more non-ionic surfactants, 2) an oil phase and 3) an aqueous phase. The amount of emulsifier present in the delivery vehicles of the present invention is from about 0.1 weight % to about 20 weight %, more preferably from about 1 weight % to about 5 weight %, and most preferably from about 1 weight % to about 2.5 weight %. The amount of oil present in the delivery vehicles of the present invention is from about 0.5 weight % to about 50 weight %, more preferably from about 5 weight % to about 30 weight %, and most preferably from about 10 weight % to about 15 weight %. The amount of water present in the delivery vehicles of the present invention is from about 30 weight % to about 99.4 weight %, more preferably from about 65 weight % to about 94 weight %, and most preferably from about 82.5 weight % to about 89 weight %. The emulsion ratio (Emul:Oil:Aq) of the delivery vehicles of the present invention ranges from about 0.1:0.5:99.4 to about 20:50:30, more preferably from about 1:5:94 to about 5:30:65, and most preferably from about 1:10:89 to about 2.5:15:82.5.

The optimal emulsion ratio can be determined by one of ordinary skill in the art through routine experimentation by obtaining penetration profiles on trial emulsions and determining which emulsion ratio maximizes the penetration of the drug substance across the stratum corneum and into the deeper skin layers.

Another consideration when optimizing the emulsion ratio of the delivery vehicles is the stability of the resultant emulsion vehicles. A stable emulsion is typically stable overnight at room temperature without any separation. More rigorous standards for stability include that the emulsion be stable for anywhere from 1 to 3 months at 43° C.

A preferred oil-in-water emulsion vehicle of the present invention includes the GDL emulsifier system, light mineral oil and an aqueous phase. In such a preferred embodiment, the preferred emulsion ratio (Emul:Oil:Aq) is 2.5:15:82.5.

The emulsion delivery vehicles of the present invention are readily prepared using art-recognized principles and methodologies in mixing the ingredients together and in choosing the type of mixing equipment to be used. The particular processing method used does not affect the penetration level of the drug across the stratum corneum and into the deeper layers of the skin. By way of example, the emulsion vehicles of the present invention can be prepared by mixing the non-ionic surfactants of the emulsifier system with the oil phase and heating the mixture to a temperature at which all chemicals are dissolved and the surfactants and oils are evenly dispersed in the mixture. Typically, the temperature ranges from about 40° C. to about 90° C., more preferably from about 50° C. to about 80° C. At the same time, the aqueous phase also is heated. The drug substance to be delivered is added to the appropriate phase based on the hydrophilic or hydrophobic nature of the drug. When the two phases are at approximately the same temperature (±5° C.), the aqueous phase is slowly added to the oil phase. The mixture is allowed to cool and the pH is adjusted to a final pH of 2 to 10, more preferably to a final pH of 3 to 8, and most preferably to a final pH of 4 to 7.5. In yet another alternative method, the oil phase is added to the aqueous phase. It is well known in the emulsion-making art that by adding water to oil smaller particles are formed, whereas by adding oil to water larger-sized particles are formed.

Alternatively, the emulsion vehicles can be prepared by first melting the non-ionic surfactants of the emulsifier system together, and second, combining the surfactants phase with the aqueous phase when the two phases are at approximately the same temperature (±5° C.), and then adding the oil phase to the suspension.

The delivery vehicles of the present invention for use in formulating compositions also may comprise one or more compounds which are selected based on the intended use of a particular composition. In general, the vehicle must be non-toxic and non-irritating to the user. The vehicle must, of course, also be compatible with the particular drug for which it will be used as a deposition vehicle. The vehicles of the present invention may be prepared and used in the form of a hand lotion, cream or other forms commonly employed in the art of cosmetics such as a fluid or "milk" emulsion, microemulsions and water-in-oil emulsions.

In addition to the compounds described above, the delivery vehicles of the present invention also may include one or more optional ingredients such as polymeric thickening agents, emollients, waxes, co-emulsifiers, lubricants, defoaming agents, preservatives, sunscreens, perfumes and colorants. These ingredients may be added to improve the general aesthetics of the compositions comprising the delivery vehicles of the present invention such as the smoothness, feel, viscosity and appearance of the compositions.

Polymeric thickening agents such as natural gums and synthetic polymers such as PEG and carbomer may be used in the vehicle formulations of the present invention as known by one of ordinary skill in the cosmetics art as viscosity increasing agents and emulsion stabilizers in hand creams and lotions. Thickening agents typically comprise in total from about 0.1 weight % to about 10 weight %, more preferably from about 0.1 weight % to about 5 weight %, and most preferably from about 0.1 weight % to about 2 weight %.

Carbomer is a preferred thickening agent in the delivery vehicles of the present invention. Carbomer which is a synthetic polymer of acrylic acid crosslinked with an allyl ether of pentaerythritol or an allyl ether of sucrose is commercially available under such brand names as CARBOPOL® (B. F. Goodrich Co., Cleveland, Ohio), ACRISINT® (3V-SIGMA, Weehawken, N.J.) and ACRITAMER® (RITA Corp., Crystal Lake, Ill.). Selection can be made in accordance with available knowledge in the art. Carbomer typically comprises in total from about 0.1 weight % to about 1 weight %, more preferably from about 0.2 weight % to about 1 weight %.

Emollients including volatile silicone oils and non-volatile emollients including highly branched hydrocarbons and mixtures thereof can be added to the vehicle formulations of the present invention. More preferably, the emollients added to the vehicles of the present invention comprise at least one volatile silicone oil and at least one non-volatile emollient. Examples of preferred volatile silicone oils useful herein include cyclomethicone, decamethylcyclohexasiloxane, hexamethyldisiloxane and mixtures thereof. Examples of preferred non-volatile emollients useful herein include dimethicone, dimethicone copolyol and mixtures thereof. Non-polar fatty acid and fatty alcohol esters useful herein include di-isopropyl adipate, isopropyl myristate, isopropyl palmitate, ethyl hexyl palmitate, isodecyl neopentanoate, $C_{12}$–$C_{15}$ alcohol benzoate, diethyl hexyl maleate, PPG 14 butyl ether and PPG-2 myristyl ether propionate. Hydrocarbons such as isohexadecane are also useful as emollients. The emollients typically comprise in total from about 0.5 weight % to about 30 weight %.

Examples of preferred waxes useful herein include ester waxes such as $C_{10}$–$C_{40}$ alcohols esterified with $C_{10}$–$C_{40}$ fatty acid, diesters of $C_{10}$–$C_{40}$ fatty acid where the alcohol is propylene glycol, ethylene glycol, polyethylene glycol, polypropylene glycol, polyglycerin, pentaerythritol tri- or tetra-esters of $C_{10}$–$C_{40}$ fatty acids, $C_{10}$–$C_{40}$ fatty acids of sorbitan tri-esters, $C_{10}$–$C_{40}$ fatty acids of sucrose polyesters having 3–8 moles of substitution, myristyl myristate, paraffin, synthetic waxes, microcrystalline waxes, castor wax, behenyl behenate and mixtures thereof.

Other surfactant-type molecules, commonly referred to as co-emulsifiers, such as cetyl stearyl alcohol (CSA) and ARLACEL-165® (a mixture of glyceryl stearate and PEG-100 stearate; ICI Americas), may be added to the formulations to increase the viscosity of the emulsion and for ease of application purposes. However, the use of such co-emulsifiers can inhibit the amount of drug transported into and through the skin. Thus, the inclusion of any such co-emulsifier in the delivery vehicles of the present invention should be tested for its effect on the penetration profile of the drug.

It is believed that the vehicles of the present invention are useful for the deposition of both hydrophilic drug substances such as synthetic amino acids, protease inhibitors and alpha-hydroxy acids including glycolic acid and lactic acid, and hydrophobic drug substances such as allantoin, melatonin, and methyl salicylate. Useful classes of compounds include vitamins, both water-soluble vitamins such as thiamin, biotin and vitamin C and oil-soluble vitamins such as vitamins A, E, D and K, topical steroids such as hydrocortisone, topical antibiotics such as erythromycin, clindamycin and tetracycline, enzymes such as collagenase, anti-fungal agents such as tolnaftate, vasodilators such as caffeine, aminophylline and theophylline, humectants such as glycerin, antiperspirants such as aluminum salts and anticholinergics such as scopolamine and atropine and keratolytics such as benzoyl peroxide and salicylic acid. Particularly useful compounds with the delivery vehicles of the present invention include zwitterions. An especially preferred class of compounds useful for deposition with the delivery vehicles of the invention comprise plasminogen activator inhibitor compounds.

The particular non-ionic surfactants used in the delivery vehicle depends upon the particular drug that one wants to deposit into the deeper skin layers. The choice of surfactants also may vary based on the hydrophilic or hydrophobic nature of the drug. In addition, the ratio of emulsifiers may vary based on the nature of the drug.

The concentration of a particular drug in the vehicles of the present invention necessary for adequate penetration can be determined by one of ordinary skill in the art through routine experimentation by obtaining penetration profiles on trial emulsions and determining which concentration of the drug maximizes the penetration of the drug substance across the stratum corneum and into the deeper skin layers. Other factors to consider when optimizing the drug concentration is the cost of the drug and the incremental therapeutic benefit achieved by the increased concentration of the drug in the vehicle. The concentration of the drug in the delivery vehicles of the present invention is from about 0.1 weight % to about 20 weight %, more preferably from about 1 weight % to about 10 weight %, and most preferably from about 1 weight % to about 5 weight %.

It is expected that the delivery vehicles and compositions of the present invention will be particularly useful in applications that are designed for use in treating humans having dry skin or other hyperkeratotic skin conditions such as acne keratoses, palmar or plantar hyperkeratosis, psoriasis, eczema, seborrheic eczema, pruritus, ichthyosis, Darier's disease, lichen simplex chronicus and inflammatory dermatoses. These conditions are typically characterized by cracking, flaking or scaling of the skin on hands, face, neck and legs.

The delivery vehicles and compositions of the present invention also are useful in applications designed to treat hyperpigmented skin conditions such as lentigines and age spots and other skin changes associated with aging such as wrinkles, blotches and atrophy or elastotic skin changes characterized by leathery changes associated with intrinsic aging or skin damage caused by extrinsic factors such as sunlight radiation, air pollution, wind, cold, dampness, heat, chemicals, smoke and cigarette smoking.

Accordingly, the active reagent used in such vehicles and compositions for such purposes may comprise one or more plasminogen activator inhibitor compounds. Plasminogen activator inhibitors capable of being deposited into and through the skin with the vehicles of the invention include natural and synthetic inhibitors such as 4-aminomethylcyclohexanecarboxylic acid, also referred to as tranexamic acid (TA), and related ω-aminocarboxylic acids such as epsilon-amino caproic acid and p-aminomethylbenzoic acid (PAMBA) as well as isomers, homologs, analogs and derivatives thereof.

Examples of synthetic inhibitors of tranexamic acid are well known in the art and include derivatives containing one or two moieties of tranexamic acid per mole of active reagent, see, e.g., Svahn et al., *J. Med. Chem.* 29:448–53 (1986), N-substituted derivatives, amides and esters of tranexamic acid, see, e.g., Okano et al., *J. Med. Chem.* 15:247–255 (1972), and cyclic derivatives containing 4, 5 or 6 carbon atom ring structures, see e.g., Dupin et al., *Pathologie Biologie* 26:233–39 (1978), all three of the above-listed references being incorporated herein by reference in their entirety.

In particular, for tranexamic acid, a 1% concentration of tranexamic acid is sufficient for adequate penetration of the drug across the stratum corneum and into the deeper skin layers. With increasing concentrations as high as 5%, one does achieve higher penetration; however, the effect is not proportional.

The following examples are merely illustrative of the scope of the present invention and are not intended as a limitation upon the scope thereof.

EXAMPLES

Materials

The synthetic non-ionic surfactant glyceryl dilaurate (GDL) was obtained from Stepan Co., Northfield, Ill. or IGI, Inc., Little Falls, N.J. and polyoxyethylene-10 stearyl ether (POE-10) was obtained from ICI Americas or IGI, Inc. Cholesterol was obtained from RITA Corp. or IGI, Inc. HEPES free acid was obtained from Sigma, St. Louis, MO. Tranexamic acid was obtained from Daiichi Pharmaceutical Co., Ltd., Tokyo, Japan. Mineral oil was obtained from Witco Corp., Petrolia, Pa. The preservatives PARAGON® and VERSENE 100® were obtained from McIntyre Group, Ltd., Chicago, Ill. and Dow Chemical, Midland, Mich., respectively. All other chemicals were of analytical grade. The water used in making the formulations was either double-distilled and deionized or deionized only.

EXAMPLE 1

Preparation of a Delivery Vehicle

A non-ionic surfactant emulsion vehicle was prepared as follows. The surfactants phase was made by mixing 9.0 weight % glyceryl dilaurate, 3.0 weight % cholesterol and 8.0 weight % polyoxyethylene-10 stearyl ether in a beaker placed on a hot plate and heated to 75° C. to melt the mixture. The melt was drawn into a syringe preheated in a 75° C. water bath. A second syringe was filled with an equal volume of a 2 weight % solution of tranexamic acid in 0.05M isotonic HEPES buffer, pH 7.4, and preheated to 70° C. The two syringes were then connected via a 3-way Teflon or metal stopcock. The aqueous buffer was then injected into the syringe containing the surfactants melt. The contents of the two syringes were mixed back and forth between the two syringes rapidly several times while the apparatus was cooled under cold tap water. This process was continued until the mixture reached room temperature. As a result of mixing equal volumes of the surfactants and aqueous phases, the final suspension contained 4.5 weight % glyceryl dilaurate, 1.5 weight % cholesterol and 4.0 weight % polyoxyethylene-10 stearyl ether. The tranexamic acid concentration of the final suspension was 1 weight %.

Oil-in-water emulsions were prepared by mixing the suspension with light mineral oil at a 85:15 ratio by weight, and the mixture was sonicated for 2 minutes to suspend the emulsion.

EXAMPLE 2

Preparation of a Delivery Vehicle

A non-ionic surfactant emulsion vehicle was prepared as follows. One thousand grams of the emulsion was made by mixing 0.5 weight % glyceryl dilaurate and 2.0 weight % polyoxyethylene-10 stearyl ether, with 15.0 weight % mineral oil in a beaker placed on a hot plate, mixed with an overhead mixer and heated to approximately 77° C. while gently mixing. The mixture was mixed until all chemicals were dissolved and the proper temperature was achieved.

In another beaker, 80.45 weight % deionized water was added, and the beaker was placed on a hot plate, mixed with an overhead mixer and heated to approximately 77° C. One weight % tranexamic acid was added to the heated water and mixed until dissolved, then 0.05 weight % citric acid was added and mixed well.

When the temperatures of the oil phase and water phase were at an approximately equal temperature (±1°–2° C.) within the temperature range of 77° C.±5° C., the water phase was slowly added to the oil phase over a period of approximately 10 minutes. The overhead mixer was adjusted to mix without aeration. The beaker containing the combined oil and water phase was removed from the heat, and the mixture was cooled while stirred. When the temperature of the mixture was below 45° C., 0.7 weight % PARAGON and 0.2 weight % VERSENE 100 were added as preservatives. The product was continually stirred until the temperature was below 30° C. The pH was adjusted to a final pH of 6.5 to 7.5 using either citric acid or sodium hydroxide as required.

EXAMPLE 3

Preparation of a Delivery Vehicle

A non-ionic surfactant emulsion vehicle for the deposition of salicylic acid is prepared as follows. The emulsion is made by mixing 1.0 weight % salicylic acid, 0.5 weight % glyceryl dilaurate, 2.0 weight % polyoxyethylene-10 stearyl ether, and 15.0 weight % mineral oil in a beaker and heating the mixture to approximately 77° C. while gently mixing.

In a separate beaker, 0.2 weight % carbomer is mixed with approximately 80.25 weight % water and heated to approximately 77° C. When the two phases are at approximately the same temperature (±5° C.), the aqueous phase is slowly added to the oil phase. The mixture is allowed to cool. When the temperature reaches below 45° C., 0.15 weight % triethanolamine (TEA) is added, then 0.7 weight % PARAGON and 0.2 weight % VERSENE 100 are added. The pH is adjusted to a final pH of 6.5 to 7.5.

Alternatively, the salicylic acid can be added to the combined oil and water phases when the mixture reaches a temperature below 45° C., before the preservatives are added and the pH is adjusted.

EXAMPLE 4

In Vivo Percutaneous Absorption of Emulsion Vehicle

Penetration profiles were obtained for tranexamic acid using three different delivery vehicles: 1) a hydroalcoholic system, 2) a non-ionic liposome system, and 3) a non-ionic surfactant emulsion system. Delivery vehicle no. 1 is a prior art formulation comprising a 10 mg/ml tranexamic acid solution of ethanol:propylene glycol:0.05M isotonic HEPES buffer, pH 7.4 (50:25:25 v/v). Delivery vehicle no. 2 was made in accordance with the method of Example 1 through the step of mixing the surfactants and aqueous phases to form liposomes; however, no oil was added to the suspension. Delivery vehicle no. 3 was made according to the method as described in Example 1 above. Approximately 2 µCi of [$^{14}$C]tranexamic acid (Amersham, Arlington Heights, Ill.) per ml of formulation was incorporated into the delivery vehicles.

Forty-five- to sixty-day-old hairless mice (SKH-HR-1; Charles Rivers Laboratories, Inc., Wilmington, Mass.) were anesthetized with sodium pentobarbital (60 mg/kg of body weight administered intraperitoneally) and maintained in an anesthetized state throughout the experiments with additional injections approximately every one and one-half hours. Formulation volumes of 50 µl were applied to a dorsal skin site of 1 cm$^2$ and the samples were left open to the atmosphere. Two sites per animal were used and tested with the same formulation. A minimum of three animals were used per formulation tested for each of the three time points 4, 8 and 12 hours following application.

At the end of the appropriate time point, the animals were sacrificed by a lethal injection of pentobarbital. The skin was carefully excised and the subcutaneous fat was removed with a dull scalpel. The excised skin section was mounted on a wooden board and stripped with Scotch 810 tape (3M, St. Paul, Minn.) at least 15 times by contacting the skin with a piece of tape of sufficient size to cover the area of the skin that was in contact with the test formulation. Strippings were carried out until the skin had a glossy appearance indicating that complete removal of the stratum corneum was achieved (usually about 20 times).

The urinary bladder and its contents were harvested and any urine excreted over the duration of the experiment was also collected. The individual strips of skin, remaining skin, urine and urinary bladder were assayed for the radiolabeled drug using a scintillation counter (Beckman LS 9000; Beckman Instruments, Fullerton, Calif.) after the addition of 15 ml of scintillation cocktail (Ecolite+; ICN Biomedicals, Irvine, Calif.).

Table 1 shows the penetration profiles for each of the delivery vehicles. Tranexamic acid is expressed as the percentage of tranexamic acid detected in the particular skin layer or bladder compared to the total amount applied. Table 1 shows data from samples collected eight hours after topical in-vivo application. The term "living skin strata (LSS)" signifies the remaining skin after the strippings comprising the viable epidermis and dermis layers of the skin.

TABLE 1

| Section | Vehicle | | |
| --- | --- | --- | --- |
| | Hydro-Alcoholic | Non-Ionic Liposome | Non-Ionic Emulsion |
| Stratum Corneum | 100.9 ± 0.96 | 97.09 ± 4.21 | |
| Living Skin Strata (LSS) | 0.03 ± 0.01 | 0.20 ± 0.07 | 0.69 ± 0.26 |
| Urinary Bladder | 0.09 ± 0.05 | 0.29 ± 0.10 | 0.52 ± 0.35 |
| LSS + Urinary Bladder | 0.12 ± 0.10 | 0.49 ± 0.09 | 1.21 ± 0.40 |
| Total Recovery | 101.0 ± 0.90 | 97.44 ± 4.30 | 97.1 ± 0.26 |

The results in Table 1 show that the non-ionic emulsion delivery vehicle best facilitates penetration of the tranexamic acid into the "biologically active" layers of the living skin strata. This vehicle also increases systemic distribution of the drug as evidenced by the increased drug concentration in the urinary bladder.

EXAMPLE 5

Effect of Cholesterol Concentration on Percutaneous Absorption

In order to evaluate the effect of cholesterol in the delivery vehicles on the absorption of tranexamic acid into and through the skin, vehicles were prepared with cholesterol (W/CHO) and without cholesterol (W/O CHO). In the vehicles without cholesterol, the amount of POE-10 was increased in the emulsifier system to compensate for the absence of cholesterol.

The emulsions were prepared by the method of Example 1 with the following exceptions. The ratio of GDL to POE-10 to CHO was either 45:40:15 (W/CHO vehicles) or 45:55:0 (W/O CHO vehicles). In all cases, the total amount of the emulsifier system in the vehicle formulations remained constant at 10 weight % throughout the experiment. The concentration of the oil in the formulations was varied from 0 weight % to 30 weight %.

Table 2 shows the penetration profiles for each of the delivery vehicles. Tranexamic acid is expressed as the percentage of tranexamic acid detected in the particular skin layer or bladder compared to the total amount applied.

TABLE 2

| Section | | Emulsion Formulations (Weight % Mineral Oil) | | | |
|---|---|---|---|---|---|
| | | 0% | 7.5% | 15% | 30% |
| Living Skin Strata | W/CHO | 0.19 ± 0.05 | 0.40 ± 0.18 | 0.69 ± 0.26 | 0.76 ± 0.27 |
| (LSS) | W/O CHO | 1.09 ± 0.42 | 1.84 ± 0.56 | 2.38 ± 0.96 | 4.41 ± 0.84 |
| Urinary Bladder | W/CHO | 0.21 ± 0.09 | 0.37 ± 0.00 | 0.52 ± 0.35 | 1.43 ± 0.39 |
| | W/O CHO | 3.23 ± 1.13 | 3.30 ± 0.66 | 5.59 ± 3.53 | 8.57 ± 1.02 |
| LSS + Urinary | W/CHO | 0.39 ± 0.12 | 0.77 ± 0.06 | 1.21 ± 0.39 | 2.20 ± 0.67 |
| Bladder | W/O CHO | 4.32 ± 1.18 | 5.14 ± 0.70 | 7.97 ± 4.03 | 12.9 ± 2.61 |
| Total Recovery | W/CHO | 99.2 ± 0.72 | 100.1 ± 0.23 | 97.11 ± 0.25 | 100.0 ± 1.31 |
| | W/O CHO | 93.30 ± 4.02 | 94.40 ± 5.27 | 91.20 ± 7.30 | 91.20 ± 10.1 |

Upon comparison of the emulsion vehicles with and without cholesterol, for example the emulsion vehicle containing 15 weight % mineral oil as set forth in Table 2 above, the data show that the inclusion of cholesterol in the delivery vehicle decreases the amount of tranexamic acid transported into and through the skin. Thus, replacement of cholesterol in the GDL emulsifier system with POE-10 increased the amount of tranexamic acid transported about 3-fold across the stratum corneum and into the living skin strata, and increased about 11-fold the systemic distribution of tranexamic acid for a combined increase in the amount transported of about 7-fold.

The increase in the amount of tranexamic acid transported with the emulsion vehicle not containing cholesterol for the other formulations with varying concentrations of mineral oil similarly increased from about 5 to 9-fold.

EXAMPLE 6

Effect of Oil Concentration on Percutaneous Absorption

As described above in Example 5, the concentration of the oil in the delivery vehicles was varied from 0 weight % to 30 weight %. The data in Table 2 shows that increasing oil concentration in the emulsion vehicles increases the total amount of tranexamic acid transported in a near-linear fashion.

EXAMPLE 7

Effect of Carbomer Concentration on Percutaneous Absorption

The emulsions were prepared by the method of Example 2 with the following exceptions. The concentration of carbomer in the formulations was varied from 0 weight % to 0.2 weight %. Carbomer was added to the Water while it was being heated and before the water phase was added to the oil phase. Approximately 7 weight % of the water was set aside to dissolve the tranexamic acid. When the temperature of the combined oil and water phases was below 45° C., 0.15 weight % triethanolamine (TEA) was added, then the TA solution, then the preservatives.

Table 3 shows the penetration profiles for each of the delivery vehicles. Tranexamic acid is expressed as the percentage of tranexamic acid detected in the particular skin layer or bladder compared to the total amount applied.

TABLE 3

| | Emulsion Formulation | | |
|---|---|---|---|
| | 7A | 7B | 7C |
| Carbomer Concentration Section | 0 | 0.2 | 0.1 |
| Living Skin Strata (LSS) | 1.89 ± 0.62 | 1.93 ± 0.42 | 3.69 ± 0.40 |
| Urinary Bladder | 3.70 ± 2.37 | 4.46 ± 0.59 | 10.53 ± 4.46 |
| LSS + Urinary Bladder | 5.59 ± 2.95 | 6.39 ± 1.03 | 14.22 ± 4.68 |
| Total Recovery | 91.99 ± 7.12 | 93.09 ± 4.36 | 96.14 ± 18.41 |

The results in Table 3 show that the inclusion of 0.1% carbomer in the vehicle formulation enhances deposition of the tranexamic acid across the stratum corneum and into the deeper layers of the skin. The results also show that the inclusion of 0.2% carbomer has no inhibitory effect on the percutaneous absorption of tranexamic acid.

The addition of carbomer to the emulsion vehicles provides improved stability; the carbomer also acts as a thickening agent in the vehicles. The 0.2 % carbomer formulation appears to be more stable than the 0.1% carbomer formulation. All three formulations were stable for a two-week period at room temperature. After two weeks, the 0.1% carbomer formulation showed some separation while the 0% and 0.2% carbomer formulations did not show any separation.

EXAMPLE 8

Preparation of Vehicle with Isopropyl Myristate

A non-ionic surfactant emulsion vehicle was prepared according to the method of Example 1 with the following exceptions. The ratio of GDL Emulsifier System (GDL:POE-10:CHO) was 57:28:15, the total concentration of the GDL Emulsifier System was 80 mg/ml, the oil used in the emulsion was isopropyl myristate and the ratio of surfactant to oil phase to aqueous phase was 8:20:71.

Table 4 compares the penetration profile of the emulsion made with isopropyl myristate to the emulsion of Example 4 made with mineral oil. Table 4 shows the penetration profiles for each of the delivery vehicles. Tranexamic acid is expressed as the percentage of tranexamic acid detected in the particular skin layer or bladder compared to the total amount applied.

TABLE 4

| | Emulsion Formulation | |
|---|---|---|
| Oil Phase | Isopropyl | Mineral Oil |
| Oil Concentration | 20 | 15 |
| Sections | | |
| Living Skin Strata (LSS) | 0.67 ± 0.14 | 0.69 ± 0.26 |
| Urinary Bladder | 1.50 ± 0.36 | 0.52 ± 0.35 |
| LSS + Urinary Bladder | 2.17 ± 0.26 | 1.21 ± 0.40 |
| Total Recovery | 95.4 ± 0.96 | 97.1 ± 0.26 |

The data shows that the penetration profiles for the amount of tranexamic acid transported across the stratum corneum and into the living skin strata of the two emulsion formulations were similar.

EXAMPLE 9

Effect of Drug Concentration on Penetration Profile

The emulsions were prepared by the method of Example 1 with the following exceptions. No cholesterol was added to the emulsion formulations. The concentration of tranexamic acid was varied from 1% to 5%. The final suspension contained 4.5 weight % glyceryl dilaurate and 5.5 weight % polyoxyethylene-10 stearyl ether.

Table 5 shows the penetration profiles for each of the delivery vehicles. Tranexamic acid is expressed as the percentage of tranexamic acid detected in the particular skin layer or bladder compared to the total amount applied as well as the actual µgs of tranexamic acid absorbed by each section.

TABLE 5

| | Emulsion Formulation | |
|---|---|---|
| Section | 1% | 5% |
| Living Skin Strata (LSS) (%) | 2.38 ± 0.96 | 1.05 ± 0.47 |
| Living Skin Strata (µg) | 11.90 ± 4.80 | 26.25 ± 11.75 |
| Urinary Bladder (%) | 5.59 ± 3.53 | 2.5 ± 1.71 |
| Urinary Bladder (µg) | 27.95 ± 17.65 | 62.50 ± 42.75 |
| LSS + Urinary Bladder (%) | 7.97 ± 4.03 | 3.55 ± 2.14 |
| LSS + Urinary Bladder (µg) | 39.85 ± 20.15 | 88.75 ± 53.5 |
| Total Recovery (%) | 91.20 ± 7.30 | 92.49 ± 4.03 |

The results in Table 5 show that although the increase in penetration of the drug into and through the skin between with the 5% TA concentration compared to the 1% TA concentration is not proportional (i.e., in terms of percentage, the 1% TA formulation absorbed 2.38% of total TA detected in the living skin strata versus 1.05% for the 5% TA formulation), the actual amount of TA absorbed with the 5% TA formulation compared to the 1% TA formulation more than doubled (e.g., the 1% TA formulation absorbed 11.90 µg in the living skin strata versus 26.25 µg for the 5% TA formulation).

What is claimed is:

1. A non-ionic surfactant emulsion vehicle comprising:

from about 0.1 to about 20 weight % of an emulsifier comprising glycerol dilaurate and polyoxyethylene-10 stearyl ether in a weight ratio from about 5:95 to about 75:25;

from about 0.5 to about 50 weight % of an oil; and from about 30 to about 99.4% by weight of water.

2. The emulsion vehicle according to claim 1 wherein the ratio of glycerol dilaurate to polyoxyethylene-10 stearyl ether ranges from about 20:80 to about 45:55.

3. A composition for enhancing the penetration of a drug substance across the stratum corneum and into deeper skin layers comprising:

from about 0.1 to about 20 weight % of an emulsifier comprising glycerol dilaurate and polyoxyethylene-10 stearyl ether in a weight ratio from about 5:95 to about 75:25;

from about 0.5 to about 50 weight % of an oil;

from about 30 to about 99.4% by weight of water; and from about 0.1 to about 20 weight % of a drug which includes a plasminogen activator inhibitor compound.

4. The composition according to claim 1 wherein the plasminogen activator inhibitor compound is tranexamic acid.

5. The composition according to claim 1 wherein cholesterol is excluded.

6. A method for enhancing the penetration of a drug substance across the stratum corneum and into deeper skin layers comprising the steps of:

providing a composition comprising:

from about 0.1 to about 20 weight % of an emulsifier comprising glycerol dilaurate and polyoxyethylene-10 stearyl ether in a weight ratio from about 5:95 to about 75:25;

from about 0.5 to about 50 weight % of an oil;

from about 30 to about 99.4% by weight of water; and from about 0.1 to about 20 weight % of a drug substance; and topically applying an effective amount of the composition to the skin.

7. Method for treating dry skin or other hyperkeratotic skin conditions comprising the steps of:

providing a composition comprising:

from about 0.1 to about 20 weight % of an emulsifier comprising glycerol dilaurate and polyoxyethylene-10 stearyl ether in a weight ratio from about 5:95 to about 75:25;

from about 0.5 to about 50 weight % of an oil;

from about 30 to about 99.4% by weight of water; and from about 0.1 to about 20 weight % of a drug which is a plasminogen activator inhibitor compound; and topically applying an effective amount of the composition to the skin.

8. A method for treating wrinkles or other skin changes associated with aging comprising the steps of:

providing a composition comprising:

from about 0.1 to about 20 weight % of an emulsifier comprising glycerol dilaurate and polyoxyethylene-10 stearyl ether in a weight ratio from about 5:95 to about 75:25;

from about 0.5 to about 50 weight % of an oil;

from about 30 to about 99.4% by weight of water; and from about 1 to about 20 weight % of a drug substance for treating wrinkles or other skin changes associated with aging; and topically applying an effective amount of the composition to the skin.

* * * * *